United States Patent [19]

Knappe et al.

[11] Patent Number: 5,169,787
[45] Date of Patent: Dec. 8, 1992

[54] TEST CARRIER FOR DETERMINING AN ANALYTE IN A BLOOD SAMPLE, PROCESS FOR MAKING THE CARRIER AND USE THEREOF

[75] Inventors: Wolfgang-Reinhold Knappe, Bürstadt; Dieter Scheithauer, Hockenheim, both of Fed. Rep. of Germany

[73] Assignee: Boehringer Mannheim GmbH, Mannheim, Fed. Rep. of Germany

[21] Appl. No.: 224,984

[22] Filed: Jul. 27, 1988

[30] Foreign Application Priority Data

Aug. 4, 1987 [DE] Fed. Rep. of Germany ....... 3725766

[51] Int. Cl.[5] ..................... G01N 31/22; G01N 33/52
[52] U.S. Cl. .................................... 436/169; 422/56; 422/57; 422/58; 427/2
[58] Field of Search ............... 436/164, 169, 170, 177; 422/56, 57, 58; 427/2

[56] References Cited

U.S. PATENT DOCUMENTS

| | | |
|---|---|---|
| 3,663,374 | 5/1972 | Moyer et al. ................ 435/301 |
| 3,791,933 | 2/1974 | Moyer et al. ................ 422/56 |
| 4,255,384 | 3/1981 | Kitajima et al. ............. 422/56 |
| 4,256,693 | 3/1981 | Kondo et al. ................ 422/57 |
| 4,312,834 | 1/1982 | Vogel et al. ................. 436/71 |
| 4,459,358 | 7/1984 | Berke .......................... 422/56 |
| 4,477,575 | 10/1984 | Vogel et al. ................. 422/57 |
| 4,604,264 | 8/1986 | Rothe et al. ................. 422/57 |
| 4,613,567 | 9/1986 | Yasoshima et al. ........... 422/57 |
| 4,820,489 | 1/1989 | Rothe et al. ................. 422/57 |

FOREIGN PATENT DOCUMENTS

| | | |
|---|---|---|
| 0016387 | 10/1980 | European Pat. Off. . |
| 0226767 | 1/1987 | European Pat. Off. . |
| 0271854 | 6/1988 | European Pat. Off. . |
| 3237233 | 2/1984 | Fed. Rep. of Germany . |
| 8402192 | 11/1983 | World Int. Prop. O. . |

OTHER PUBLICATIONS

Ikeda, English Language Abstract of 62-116258, Japanese Patent, vol. 11, No. 334 (P-631) (2781) Oct. 31, 1987.

Primary Examiner—Jill A. Johnston
Attorney, Agent, or Firm—Felfe & Lynch

[57] ABSTRACT

The present invention provides a test carrier for the determination of an analyte from whole blood with the help of reagents contained in the test carrier, said test carrier having a blood application side to which blood is applied, an evaluation side on which, as a result of the reaction of the reagents with the analyte, an optically detectable change takes place, and an erythrocyte separation means between the blood application side and the evaluation side, wherein the erythrocyte separation means includes an integral composite having a first zone, which contains a polymeric film former, kieselguhr and a pigment, and thereupon, with formation of a transition region, a second zone containing a polymeric film-former, formed by liquid coating the first zone facing the blood application side and the second zone facing the evaluation side of the integral composite. The present invention also provides a process for the production of this test carrier and a method for analyzing blood samples using it.

16 Claims, 1 Drawing Sheet

TEST CARRIER FOR DETERMINING AN ANALYTE IN A BLOOD SAMPLE, PROCESS FOR MAKING THE CARRIER AND USE THEREOF

The present invention is concerned with a test carrier for the determination of an analyte from whole blood with the help of reagents contained in the test carrier, said test carrier having a blood application side, to which blood is applied, an evaluation side, on which, as a result of the reaction of the reagents with the analyte, an optically detectable change takes place, and an erythrocyte separation means between the blood application side and the evaluation side. The present invention is also concerned with a process for the production of such a test carrier.

For the qualitative or quantitative analytical determination of components of blood, in recent times so-called carrier-bound tests have increasingly been used. In the case of these carrier-bound tests, reagents are embedded in appropriate layers of a solid test carrier which is brought into contact with the sample. The reaction of sample and reagents leads to an optically detectable change, especially to a colour change, which can be evaluated visually or with the help of a device, usually reflection-photometrically. Instead of a colour change, the reaction can also give rise to the formation of or to the change of another optically detectable signal, for example a fluorescence or a luminescence.

Test carriers are frequently formed as test strips which consist essentially of a longitudinal support layer of synthetic resin material with test fields applied thereto. However, test carriers are also known which are formed as quadratic or rectangular platelets.

Carrier bound tests are characterised especially by the simplicity of the handling. It is all the more regretable that, with most of the previously known carrier bound tests, the blood cannot be used directly as so-called whole blood. On the contrary, it is necessary to separate off the red blood corpuscles (erythrocytes) in order to obtain colourless plasma or serum. This usually takes place by centrifuging, i.e. an additional handling step is necessary. Furthermore, a device for centrifuging is not available everywhere since carrier bound tests are, to an increasing extent, also made available to lay persons. Centrifuging requires a relatively large amount of sample, whereas, on the other hand, the endeavour in clinical diagnosis is to suffice with a small blood droplet such as can be obtained by a prick in the finger.

Therefore, attempts have not been lacking to make available test carriers which make possible analytical determination directly from blood.

Thus, from DE-B 1 598 153 and corresponding to U.S. Pat. No. 3,630,957 a test carrier is known with a film layer produced from an aqueous dispersion of natural or synthetic polymers in which are present the reagents necessary for the detection. With this test carrier, certain analytical determinations, especially the determination of glucose, can be carried out directly from the blood. However, in the case of other analytical determinations, good results are not obtained with such test carriers, which may be due to the fact that the component materials of the sample cannot penetrate into the film in sufficient amount.

From EP-A-16 387 and corresponding U.S. Pat. No. 4,312,834 is known a test carrier layer also based upon the use of a dispersion film former which avoids this problem in that it contains relatively large amounts of (especially inorganic) small particles. With this there is obtained a universally usuable test layer which, however, does not permit a determination from whole blood because not only comparatively large sample components to be analysed but also erythrocytes can penetrate into this layer unhindered.

From EP-A-45 476 and corresponding U.S. Pat. No. 4,477,575 it is known to use glass fibres for obtaining serum or plasma on a test carrier. This solution of the problem is universally usable but it is necessary to apply the glass fibre layers to the test carrier in an appropriate way. A comparatively complicated test carrier construction thereby results and the production process is expensive.

Also, insofar as hitherto test carriers of the initially described type have been suggested, in which, on one side, blood can be applied without previous erythrocyte separation and the evaluation takes place on the other side, an erythrocyte separation means thereby being present between the blood application side and the evaluation side, these attempts have not proved to be satisfactory.

In U.S. Pat. No. 3,663,374 and in U.S. Pat. No. 4,256,693, a membrane filter is used in order to prevent the passage of the erythrocytes from the blood application side to the evaluation side. In principle, membrane filters are admittedly suitable for filtering off erythrocytes. However, the use thereof in test carriers has not been successful. The same applies to the combination of the membrane filter with a pre-positioned glass fibre layer, also mentioned in these U.S. Patents, which is to prevent the blockage of the membrane filter with coarser particles. The production of such test carriers would be very expensive without a satisfactory function being achieved.

In U.S. Pat. No. 4,069,817 and several other US Patents of the same Applicant, there is also discussed the possibility of providing in a test carrier an intermediate layer for preventing the passage of erythrocytes which, at the same time, contains light-blocking components in order to ensure that the light beams of the evaluation device cannot penetrate into the erythrocyte-containing layer. However, this Patent does not describe how the filtering of the erythrocytes could be achieved.

Therefore, it is an object of the present invention to provide a test carrier with which the carrying out of medical-diagnostic determinations is possible directly from whole blood, the test carrier thereby being easy to handle and simple and economic to procedure.

Thus, according to the present invention, there is provided a test carrier for the determination of an analyte from whole blood with the help of reagents contained in the test carrier, said test carrier having a blood application means, to which blood is applied, an evaluation means, in which, as a result of the reaction of the reagents with the analyte, an optically detectable change takes place, and an erythrocyte separation means in the fluid path between the blood applications means and the evaluation means, wherein the erythrocyte separating means includes composite structure having a first zone, which contains a polymeric film former, kieselguhr and a pigment, and thereupon, with formation of a transition region, a second zone, containing a polymeric film former, formed by liquid coating the first zone. With respect to the fluid path of the sample in the test carrier the first zone is directed towards the blood application means and the second zone is directed towards the evaluation means and each of such zones is -at least in use of the test carrier- in fluid communication with the corresponding means.

By means of the present invention, a test carrier is provided for whole blood analysis, which comprises an erytrhocyte retention means which is formed by a process which is easy to carry out. passage of the plasma from the first zone into the evaluation zone takes place in a few seconds so that a rapid evaluation is possible. Handling is simple, especially since the applied blood does not have to be wiped off or washed off, as was frequently necessary in the case of previously known test strips.

The process according to the present invention for producing such a test carrier requires two different coating masses which, in separate coating steps, form a thin layer. Besides a polymeric film former dispersed or dissolved in the carrier liquid, the first coating mass contains kieselguhr, a pigment and known adjuvant materials, for example buffers, wetting agents, thickening agents, defoamers and the like. The second coating liquid also contains a dispersed or dissolved polymeric film former.

For the production of an integral composite structure consisting of a first zone and a second zone, the first coating mass first forms a thin layer on a substrate base and is dried. Thereafter, on this layer, the second coating mass forms a thin layer and dries, components of the second coating liquid thereby penetrating into the first formed layer. Therefore, the first zone and the second zone are not separated from one another by a sharp boundary but rather form an integral structure with a transition region.

Preferred polymeric film formers include organic synthetic resins, such as polyvinyl esters, polyvinyl acetates, polyacrylic esters, polymethacrylic acid, polyacrylamides, polyamides an polystryrene. Apart from homopolymers, there are especially also preferred copolymers, for example of butadiene and styrene or of maleic acid esters and vinyl acetate, as well as terpolymers. However, further film-forming, natural or synthetic organic polymers, as well as mixtures thereof, can also be used. Gelatine is not suitable.

The film formers can be dissolved in appropriate organic solvents. It is often advantageous to use a dispersion of an appropriate film former, in which case the preferred carrier liquid is water.

Dispersion film formers contain submicroscopic polymer particles insoluble in the carrier liquid which are dispersed in very fine distribution in the carrier liquid. If, during film formation, the liquid is removed by evaporation or volatilisation, then the particles approach one another and finally touch. Due to the thereby occurring large forces and an increase of surface energy involved with the film formation, the particles grow together to give a substantially unbroken film layer. Further details in this regard are to be found, for example, in the article "Latex Film Formation", by J. W. Vanderhoff in Polymer News, 1977, pages 194–203.

Kieselguhr is also called diatomaceous earth. This is a deposit, resulting from the silicic acid structures of types of diatoms, which is mined in various places. The kieselguhr preferably used has an average particle diameter of 5–15 μm., these values being determined with a laser granulometer such as "Type 715" which is marketed by the firm Pabisch, München, FRG.

The pigment preferably consists of particles with an average diameter of from about 0.2 to 0.7 μm. Titanium dioxide is, for example, especially preferred. However, other pigments can also be used, the particle sizes of which usually lie substantially in the given range, which correspond approximately to the wavelength spectrum of visible light. A maximum light scattering and thus a highly covering pigment is thereby achieved.

The reaction time in the laminated composite is shortened when this preferably has a maximum thickness of 0.6 mm. and especially preferably a maximum thickness of 0.2 mm.

As substrate for the forming of the first coating mass, there can be used, for example, a plate of glass or of another material from which the film layer can easily be removed. It is thereby possible to remove the finished laminated composite and, for example, to mount it on a transparent support film, the evaluation side thereby facing the support film so that the blood application side of the laminated composite is freely accessible.

Substantially simpler in the production and, therefore, preferred is the fixing of the composite on to a porous support layer, the blood application side thereby facing the support layer. This is preferably achieved by the direct use of the porous support layer as substrate for the forming of the first coating mass. In the case of such an integral composite, a free entry of air to the detection zone is possible, the reaction time in this zone thereby being considerably shortened in many cases. End point determinations are thereby possible.

As porous support layer, there can, in principle, be used any porous support structure, i.e. any structure that is flat and enables quick or rapid penetration of blood. A sieve-like structure of a synthetic resin material with very many holes arranged close to one another could, for example, be used. Preferably, however, the porous support consists of a textile material and especially of a woven or knitted fabric, which can be produced, for example, from polyamide, polyester or silk. A fleece or paper can possibly also be used. Appropriate materials are described in EP-A-113 896.

The present invention will now be described in more detail in the following on the basis of embodimental examples illustrated schematically in the Figures, wherein.

Figure 1:
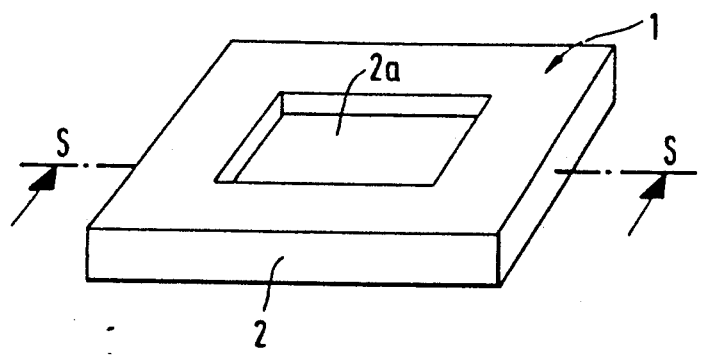
FIG. 1 is a perspective illustration of a test carrier according to the present invention.

The test carrier 1 illustrated in FIG. 1 consists essentially of a frame 2 produced, for example, from a synthetic resin and a multi-layer test field 2a enclosed in this frame.

The multi-layer test field 2a consists, in the illustrated case, in cross-section, of an integral composite structure 3 acting as an erythrocyte separation means and a porous support layer 4. The integral composite 3 includes a first zone 5 and a second zone 6, as well as a transition region 7 between the two zones indicated by a broken double line. The porous support layer 4 faces the blood application side 8 of the integral composite 3, whereas the second zone 6 faces the evaluation side 9.

The multi-layer test field 2a can, of course, contain further layers. The illustrated example is especially simply constructed insofar as the first zone 5 and the second zone 6 simultaneously contain the reagents for the detection reaction. However, it can also be desirable to separate the functions of "erythrocyte separation" and "detection reaction" and to provide additional layers for the latter, especially on the detection side but possibly also on the blood application side.

For carrying out an analytical determination, a possibly pre-measured amount of blood is applied to the blood application side 8, the test carrier thereby usually being held with this side upward. The blood penetrates through the porous carrier layer 4 into the base zone 5. Because of the construction according to the present invention of the integral composite structure, upon further penetration, the erythrocytes remain behind so that no red blood coloured matter enters the detection zone 6. The optical evaluation takes place from the evaluation side 9. The pigment thereby blocks the illumination to such an extent that it cannot penetrate into the region of the integral composite structure in which red blood coloured matter is present. Consequently, the analysis is not falsified.

The integral composite according to the present invention thus achieves, in its totality, what is required, for example, in the above-mentioned U.S. Pat. No. 4,069,817, without appropriate means being stated, namely, filtering off the erythrocytes from the penetrating blood sample and, at the same time, so blocking the light illumination necessary for the optical evaluation that it does not penetrate into the region of the integral composite structure in which red blood coloured matter is present.

Details of how the filter action is achieved have not been completely elucidated. On the one hand, it can be ascertained that a layer having the composition of the first zone 5 (for example applied to a porous support layer) does not have sufficient erythrocyte separating properties. On the other hand, it can be ascertained that a considerable part of the second coating mass, in the case of the forming on the underlying layer, penetrates into this. Thus, it is to be assumed that the particles of the dispersed or dissolved polymer from the second coating mass penetrate into the previously produced layer, a gradient of the polymer thereby being adjusted in the transition region 7 between the second zone 6 and the first zone 5. It is to be assumed that the comparatively open structure of the first zone 5 is thereby just closed to a sufficient extent that, on the one hand, the erythrocytes are held back but that, on the other hand, even comparatively large components of the sample to be analysed can penetrate into the second zone 6.

Details of the chemical course of the analytical determination are not important for the present invention. It is only important that the optically detectable change characteristic for the concentration to be determined takes place in the second zone 6 or in a further layer of the test carrier arranged on the same side of the transition region 7 and not in the first zone 5. In the case of numerous test processes usual in clinical chemistry, as concluding step there is formed, for example, a coloured substance (for example from a chromogenic substrate of an enzyme participating in the reaction) or a coloured substance is reacted so that it changes its color. Such a reaction component can be designated "an optically detectable signal-producing component" or briefly also a signal-producing component (SPC).

Such a component is preferably present in the second zone 6 of the integral composite structure 3. It is preferably contained in the second coating mass. However, it is also possible subsequently to impregnate or spray the second zone 6 with an SPC, this being especially preferred when the second coating mass is produced from a dissolved organic film former.

However, the SPC is not necessarily present initially in the second zone 6. On the contrary, it is known to carry out tests in which such components are formed or are present in another layer of a multi-layer test carrier and, in the course of the reaction, pass into the actual detection region. The present invention is also applicable to such processes, in which the components can initially be contained in the first zone 5, in the porous support layer 4 or in a further layer arranged in front.

In detail, the integral composite structure according to the present invention is preferably produced in such a manner that the first coating mass is first applied to a slowly moving strip of a material appropriate as porous support layer 4 over the full breadth of the strip. The coating mass thereby has a somewhat honey-like viscosity so that it remains preponderantly on one side of the textile support layer material but sinks into the intermediate spaces between its preferably multifilar threads. In the case of the finished product, from the direction of the blood application side, the material of the first zone is to be recognised in the intermediate spaces of the textile structure but it should not completely envelop the threads thereof.

The connection between the support layer and the coating forming the first zone is so firm that it cannot be separated without destruction.

The greater is the proportion of pigment in the first coating mass, the better are the erythrocytes retained but also the more slowly the plasma penetrates into the evaluation zone. In the first coating mass, the kieselguhr and the pigment are preferably in a weight ratio of 1:0.5 to 1:2 and especially preferably in a weight ratio of 1:0.8 to 1:1. A corresponding weight ratio is then, of course, also obtained in the first zone 5. In this regard, it is to be noted that all concentration statements of the zones 5 and 6 refer to the parts thereof lying outside of the transition region 7.

The kieselguhr and the polymeric film former in the first coating mass and consequently also in the first zone 5 are preferably in a weight ratio of 1:0.2 to 1:0.9 to one another.

After the application of the first coating mass, this forms a thin layer. Preferably a socalled "rake", i.e. a doctor blade, is arranged over the transported strip of porous support layer in order to adjust the desired layer thickness.

Correspondingly, in a second working step, which is preferably completely separate from the first one because of the necessarily comparatively long drying times, on to the composite of porous support layer and the layer arranged thereon from the first coating mass, there is applied the second coating mass in corresponding manner. This second layer should be applied very thinly. The more polymer is applied, the more strongly are the erythrocytes held back. At the same time, however, a slower formation of the optical signal is to be observed with more polymer. The polymeric film former in the second coating mass is preferably applied with a maximum weight per unit surface area of 200 g./m$^2$.

As mentioned above, in practice it has been shown that the second coating mass penetrates to a considerable extent into the underlying layer. Thus, for example, in the case of an adjusted height of the coating gap of 10μ, a consumption of second coating mass was found which corresponds to a layer of 50μ thickness.

The quality of the final product is also influenced by the viscosity of the coating masses. Preferably the first coating mass has a viscosity of 300 to 3000 mPas (millipascal seconds) measured at a shear gradient of 492 $s^{-1}$ according to the German "Deutsche Industrienorm" DIN 53019. The second coating mass preferably has a viscosity of 10 to 1000 mPas at the same conditions of measurement.

Figure 3:
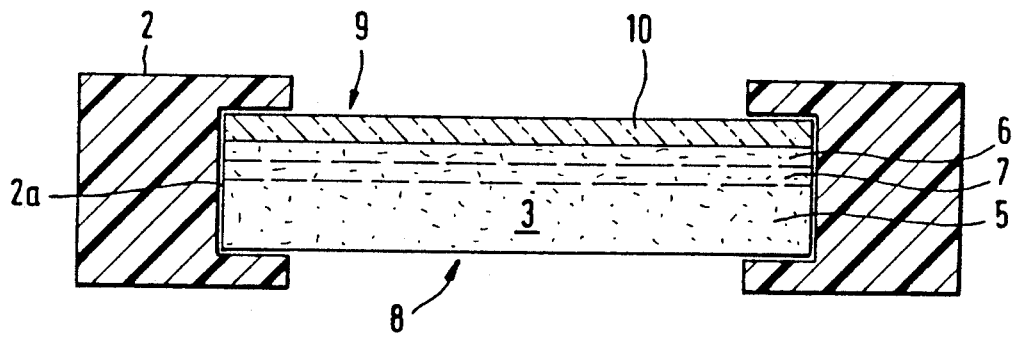
FIG. 3 is a section corresponding to FIG. 2 but with an alternative layer construction.

As mentioned above, the integal composite structure 3 can also be produced, for example, on a glass plate from which it can easily be removed after the production. Since, however, it is not mechanically stable, it is preferable to apply it to a support material. FIG. 3 shows an alternative embodiment of a test carrier according to the present invention, in which, as support material, a transparent film 10 is used which is stuck to the second zone 6. Such an embodiment can be preferable in cases in which the porous support layer 4 would disturb.

The laminated composite according to the present invention can be used in test carriers of greatly differing external construction.

All that is important is that the blood is supplied to the first zone 5 and that the evaluation takes place on the side of the second zone 6. Otherwise, however, numerous further constructional features, layers or reagents can be used.

Figure 4:
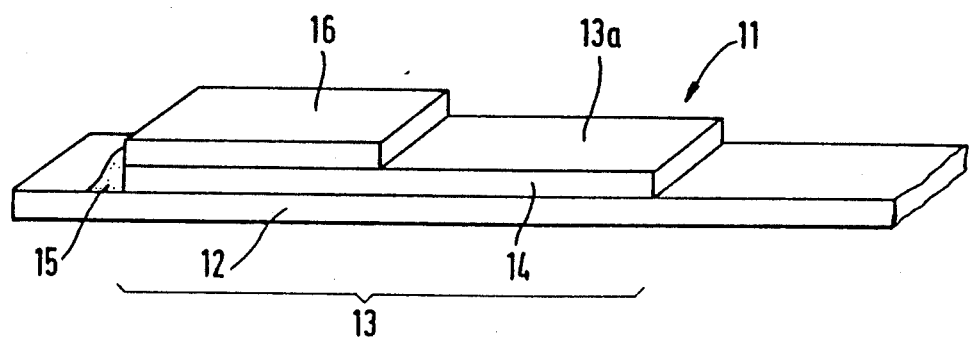
FIG. 4 is a perspective illustration of an alternative embodiment of a test carrier according to the present invention.

FIG. 4 shows, for example, a test carrier 11 formed similary to a conventional test strip with a narrow, longitudinally extending base film 12 which serves for handling.

Figure 2:
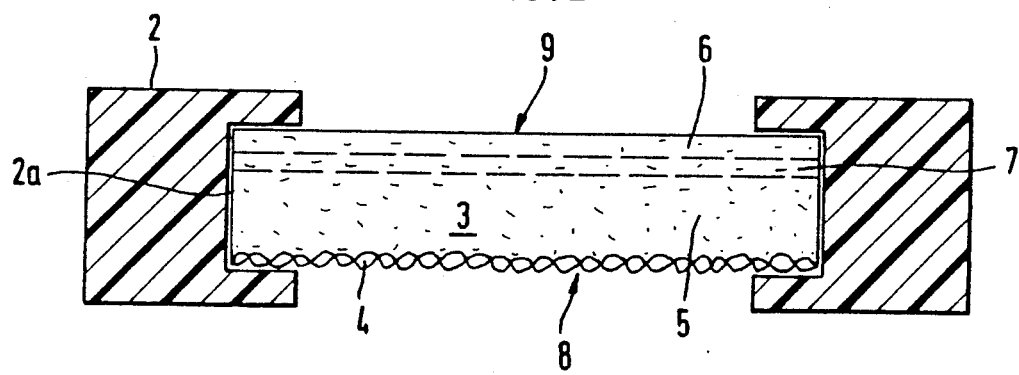
FIG. 2 is a section through the test carrier according to FIG. 1 along the line S/S.

On the base film 12 is to be seen a test zone 13 in which a liquid transport layer 14 is stuck, for example, with a melt adhesive strip 15 to the base film 12. The liquid transport layer 14 is partly covered over by a test field 16 which, in cross-section, is constructed corresponding to test field 2a in FIG. 2. With the porous support layer 4 downwardly, it is so fixed by means of the melt adhesive strip 15 to the base film 12 that it is in liquid contact with the liquid transport layer 14.

In the case of the test carrier illustrated in FIG. 4, the blood sample is applied to the region 13a of the liquid transport layer not overlapped by the integral composite 16 and penetrates from there into the liquid transport layer (by the action of capillary force) in the region under the composite laminate 16 so that the blood can penetrate into the first zone of this laminated composite 16.

The construction illustrated in FIG. 4 has the advantage that the blood application and the evaluation take place from the same test carrier side.

The invention is used especially advantageously in combination with the test carrier construction described in German Patent Application 36 43 516, reference being made to the full content of this Patent Application.

The following Examples are given for the purpose of illustrating the present invention:

EXAMPLE 1

Production of a test field for a test carrier for the detection of glucose in blood

| | |
|---|---|
| 198 g. | acrylic acid ester co-polymer dispersion (Acronal 14D of BASF, Ludwigshafen, Federal Republic of Germany, 55% in water) |
| 174 g. | swollen, highly viscous methylhydroxyethylcellulose (0.5% in water) |
| 336 g. | kieselguhr |
| 336 g. | titanium dioxide |
| 0.95 g. | tetraethylammonium perfluorooctanesulphonate |
| 40 g. | 0.5M phosphate buffer, pH 5.5 |
| 23 g. | methanol |
| 46 g. | 1-hexanol |
| 69 g. | acetone |
| 65 g. | water | are worked up to give a homogeneous first coating mass and coated on to a 0.20 mm. thick polyester filter fabric (2 F 777, Schweizer Seidengazefabrik Thal, Switzerland) with 0.18 mm. gap height and dried.

On to the so obtained coated carrier is applied a second coating mass consisting of

| | |
|---|---|
| 102 g. | acrylic acid ester co-polymer dispersion (Acronal 14D of BASF, 55% in water) |
| 38 g. | swollen, highly viscous methylhydroxyethylcellulose (0.5% in water) |
| 3 g. | sodium dodecylbenzenesulphonate |
| 36 KU | glucose oxidase |
| 1050 KU | peroxidase |
| 1.48 g. | 3,3',5,5'-tetramethylbenzidine |
| 0.53 g. | 1-phenylsemicarbazide |
| 28 g. | 1-methoxy-2-propanol |
| 40 g. | 1-hexanol |
| 38 g. | water | which had been worked up to a homogeneous mass, with 0.02 mm. gap height and dried.

The so obtained laminated composite is used in a test strip according to FIG. 4 and gives a good gradation in the concentration range of 20–250 mg. glucose/dl. in the case of the use of whole blood.

EXAMPLE 2

Production of a test field for a test carrier for the detection of triglycerides in blood

| | |
|---|---|
| 37 g. | polyvinyl propionate dispersion (50% in water) |
| 29 g. | swollen, highly viscous methylhydroxyethylcellulose (0.5% in water) |
| 56 g. | kieselguhr |
| 56 g. | titanium dioxide |
| 3.2 g. | sodium dodecylbenzenesulphonate |
| 40 g. | 0.5M phosphate buffer, pH 5.5 |
| 3.8 g. | methanol |
| 7.7 g. | 1-hexanol |
| 11.5 g. | acetone |
| 22 g. | water | are worked up to give a homogeneous first coating mass and coated with 0.15 mm. gap height on to a 0.09 mm. thick pure silk fabric (Type 541 of the Spinnhütte Seidentechnik, Celle, Federal Republic of Germany) and dried.

To the so obtained carrier is applied a second coating mass, consisting of

| | |
|---|---|
| 20 g. | polyvinyl propionate dispersion (50% in water) |
| 0.28 g. | sodium alginate |
| 70 g. | 0.2M phosphate buffer, pH 7.5 |
| 0.58 g. | adenosine-5'-triphosphate, disodium salt |

| | |
|---|---|
| 0.59 g. | magnesium sulphate heptahydrate |
| 1.0 g. | dioctyl sodium sulphosuccinate |
| 0.45 g. | 3,3',5,5'-tetramethylbenzidine |
| 15 mg. | 1-(4-methylphenyl)-semicarbazide |
| 16.4 g. | 1-hexanol |
| 30 g. | acetone |
| 2.0 g. | Triton X-100 |
| 27 KU | cholesterol esterase |
| 8.0 KU | glycerol phosphate oxidase |
| 27 KU | glycerokinase |
| 73 KU | peroxidase |
| 50 g. | water, | which had been worked up to a homogeneous mass and the pH of which had been adjusted to 7.5, with 0.01 mm. gap height and dried.

After dropping blood on to the fabric side, the test fields so obtained give a good gradation in the concentration range of 100-300 mg. triglyceride/dl.

EXAMPLE 3

Production of a test field for a test carrier for the detection of glucose in blood To 46.3 g of a 20% by weight solution of polyvinyl acetate (Mowilith 70 of the firm Hochst AG) in acetone/1-hexanol/methanol (3:2:1, v/v/v) is added a solution of 1.30 g. dioctyl sodium sulphosuccinate in 29.4 g. acetone. 28 g. kieselguhr and 28 g. titanium dioxide are dispersed in this mixture. With this homogeneous first coating mass, a 0.20 mm. thick polyester filter fabric (2 F 777, Schweizer Seidengazefabrik Thal, Switzerland) is coated with a gap height of 0.2 mm. and dried.

On to the so obtained coated carrier is applied a second coating mass consisting of

| | |
|---|---|
| 64 g. | of a 20% weight solution of polyvinyl acetate (Mowilith 70) in acetone/1-hexanol/methanol (3:2:1 v/v/v) |
| 1.3 g. | dioctyl sodium sulphosuccinate |
| 36 g. | acetone |
| 264 mg. | 1-phenyl semicarbazide |
| 740 mg. | 3,3',5,5'-tetramethylbenzidine |
| 13.8 g. | 1-methoxy-2-propanol | which had been worked up to give a clear, viscous solution, with a gap height of 0.04 mm. and dried.

On to the so obtained test field can be applied the reagents a) by a further coating or the reagents b) by spraying:
  a) The coating mass for the coating consists of
    20 g. swollen, highly viscous methylhydroxyethylcellulose (0.5% in water)
    36 kU glucose oxidase
    1050 kU peroxidase
    and is applied with a gap height of 0.02 mm. and dried.
  b) The spray solution consists of
    72 kU glucose oxidase
    2.1 MU peroxidase
    40 ml. water
    and is sprayed on in an amount of 20-30 ml./m² and dried.

Upon dropping blood on to the fabric side, the so obtained test fields give a good gradation in the concentration range of 150-600 mg. glucose/dl.

It will be understood that the specification and examples are illustrative but not limitative of the present invention and that other embodiments within the spirit and scope of the invention will suggest themselves to those skilled in the art.

We claim:

1. Test carrier for determination of an analyte in a whole blood sample comprising a two sided erythrocyte separation means, a first side of said erythrocyte separation means being in fluid communication with a means for the application of blood and a second side of said erythrocyte separation means being in fluid communication with an evaluation means, said erythrocyte separation means comprising an integral composite structure having a first zone, a second zone and a transition region between said first and second zones, said first zone containing a polymeric film former, kieselguhr and a pigment, said first zone having applied thereon said second zone containing a liquid coated polymeric film former thereby forming said transition region of said integral composite structure between said first and second zones, said first zone of said erythrocyte separation means facing said first side and said second zone of said erythrocyte separation means facing said second side.

2. Test carrier of claim 1, wherein said integral composite structure further comprises a porous support layer to which said first zone is fixed, said support layer facing said first side of said erythrocyte separation means.

3. Test carrier of claim 1, wherein at least one of the polymeric film former of said first zone and said second zone is a dispersion film former.

4. Test carrier of claim 1, wherein said kieselguhr has an average particle diameter of from 5 to 15 um.

5. Test carrier of claim 1, wherein said pigment has an average particle diameter of from 0.2 to 0.7 um.

6. Test carrier of claim 1, wherein said kieselguhr and said pigment in said first zone are in a weight ratio of from 1:0.5 to 1:2.

7. Test carrier of claim 1, wherein said kieselguhr and said polymeric film former of said first zone are in a weight ratio of from 1:0.2 to 1:0.9.

8. Test carrier of claim 1, wherein said integral composite structure has a thickness of up to 0.6 mm.

9. Test carrier of claim 1, wherein said integral composite structure has a thickness of up to 0.2 mm.

10. Process for producing a test carrier for determining an analyte in a sample of whole blood, comprising:
    forming a first zone of an integral composite structure by applying a first flowable coating mass to a substrate base, said first coating mass containing a solution or dispersion of a polymeric film former in a carrier liquid, kieselguhr, a pigment and an adjuvant and drying said first coating mass to form a first zone on said substrate base, applying a second coating mass containing a solution or dispersion of a polymeric film former to said film to form a second zone, said first zone and second zone forming an integral composite structure with a transition region formed therebetween, and positioning said laminated composite structure in a test carrier such that the first zone is in fluid communication with a blood application means of said carrier and the second zone is in fluid communication with an evaluation means of said test carrier.

11. Process of claim 10, wherein said substrate base is made of a porous material.

12. Process of claim 10, wherein said second coating mass further comprises a component which produces an optically detectable signal in a reaction involving said analyte.

13. Process of claim 10, wherein said first coating mass has a viscosity of 300 to 3000 millipascal seconds at a shear gradient of $492 s^{-1}$ according to DIN 53019.

14. Process of claim 10, wherein said second coating mass has a viscosity of 10 to 1000 millipascal seconds at a shear gradient of $492 s^{-1}$ according to DIN 53019.

15. Process according to claim 10, wherein said second layer has a maximum weight of 100 g of polymeric film former per $m^2$.

16. Method for determining an analyte in a whole blood sample comprising contacting said sample with a test carrier of claim 1 and determining a reaction between a reagent and said analyte as an indication of said analyte.

* * * * *